United States Patent [19]

Söhn

[11] Patent Number: 5,762,712
[45] Date of Patent: Jun. 9, 1998

[54] SPRINKLING DEVICE FOR METERED APPLICATION OF SUPER ABSORBING SWELLING SUBSTANCES

[75] Inventor: Hans-Werner Söhn, Ochtendung, Germany

[73] Assignee: Winkler & Dünnebier Maschinenfabrik und Eisengiesserei KG, Neuwied, Germany

[21] Appl. No.: 695,314

[22] Filed: Aug. 9, 1996

[30] Foreign Application Priority Data

Aug. 22, 1995 [DE] Germany ............ 195 30 771.2

[51] Int. Cl.[6] ........................................... B05C 3/12
[52] U.S. Cl. ................ 118/419; 198/540; 198/544; 198/550.01; 198/550.9
[58] Field of Search ........................ 239/668, 669; 198/311, 359, 360, 540, 544, 547, 550.01, 550.2, 550.9, 550.13, 560, 562; 118/308, 419, 324

[56] References Cited

U.S. PATENT DOCUMENTS

| | | | |
|---|---|---|---|
| 3,707,222 | 12/1972 | Hartley | 198/547 |
| 4,257,518 | 3/1981 | Stock et al. | 198/544 |
| 4,921,089 | 5/1990 | Teske | 198/534 |
| 5,415,717 | 5/1995 | Perneborn | 118/308 |

*Primary Examiner*—Donald E. Czaja
*Assistant Examiner*—Calvin Padgett
*Attorney, Agent, or Firm*—Collard & Roe, P.C.

[57] ABSTRACT

A sprinkling device for applying powdery to granulated materials, particularly super-absorbing swelling substances (SAP-material) to a continuously moving material web in the manufacture of suction cores for sanitary napkins, disposable diapers, etc. The SAP-material is withdrawn from a supply container by a toothed belt of a conveyor system. The toothed belt has conveying troughs of varying shapes to enable an exact volumetrically metered amount of SAP-material to be disposed onto a predetermined surface of the material web.

12 Claims, 5 Drawing Sheets

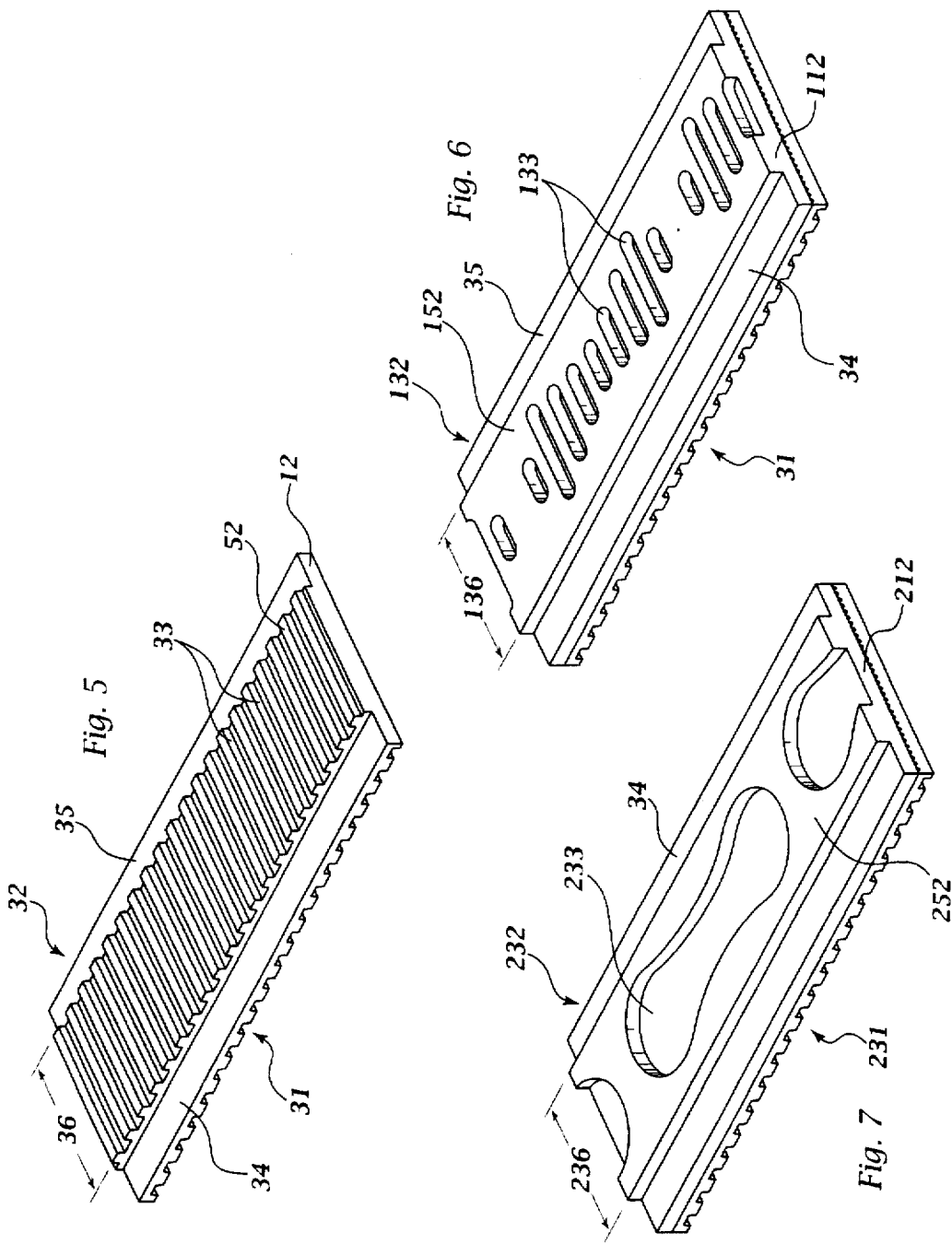

SPRINKLING DEVICE FOR METERED APPLICATION OF SUPER ABSORBING SWELLING SUBSTANCES

BACKGROUND OF THE INVENTION

1. Field of the Invention

The present invention relates to sprinkling devices. More particularly, it relates to a sprinkling device for the metered application of powdery to granulated super-absorbing swelling substances (hereinafter referred to as SAP-materials) to predetermined surfaces.

2. The Prior Art

In order to enhance the absorbing power, liquid retention capability and also the possibilities for designing hygienic products such as disposable diapers, sanitary napkins for women, slip inserts, etc., SAP-materials are usually embedded in the absorbing core of such products. The absorbing core of these products is generally formed from absorbing fibers, such as, for example, cellulose.

SAP-materials are commercially available in a granulated and a powder form. The processing of SAP-materials in hygienic products requires an exact metering in a defined amount per product. This metering assures a certain absorption and retention capability of the product.

In addition, depending on the product, it is also necessary that the distribution of the SAP-material within the product is exactly maintained. When using SAP-material in modern "airlaid products", the distribution over a defined area must be as uniform as possible.

SUMMARY OF THE INVENTION

The present invention provides an improved sprinkling device for the metered application of powdery to granulated materials such as super absorbing swelling substances (SAP-material), to predetermined surfaces of a continuously moving web of material within a machine for manufacturing hygienic products According to the invention, the machine for manufacturing hygienic products has a conveyor system, a conveyor drive, a supply container having an open bottom side disposed above the conveyor system, and a housing for supporting the supply container and enclosing the conveyor system. The housing has an SAP-material discharge slot directed at the moving web of material. The conveyor system has at least two cogs spaced from each other on opposite sides of the open bottom of the supply container, and a belt coupled around the two cogs. The belt has two opposite lateral edges, a geared driving surface for engaging each of the cogs, and a conveying surface. The conveying surface has conveying troughs for receiving and transporting the SAP-material from the supply container to the discharge slot. The conveying troughs are varied in size, shape, and depth to enable a volumetrically exact dispensing of SAP-material onto the material web.

A pair of slide guides help support and guide the conveyor system belt to carry the metered amount of SAP-material to the discharge slot. In addition, the slide guide for lateral seals along the recessed lateral edges of the belt. A cleaner scraper is provided on an inside wall of the supply container such that it is disposed facing opposite the direction of the belt movement. The cleaner scraper prevents accidental discharge of SAP-material through the discharge slot, and ensures the proper filling of the conveyor troughs before passing beyond the supply container opening.

It is therefore an object of the present invention to provide a sprinkling device for dispensing SAP-material onto a continuously moving web of material for producing suction cores for sanitary napkins.

It is another object of the invention to provide a sprinkling device for intermittently or continuously dispensing volumetrically exact amounts of SAP-material to a continuously moving web of material.

It is a further object of the invention to provide a sprinkling device for intermittently or continuously dispensing volumetrically exact amounts of SAP-material to a continuously moving web of material such that a quick exchange of the format or worn parts is easily facilitated.

It is another object of the invention to provide a sprinkling device for dispensing SAP-material onto a continuously moving web of material for producing suction cores for sanitary napkins that is easily and cheaply manufactured.

BRIEF DESCRIPTION OF THE DRAWINGS

Other objects and features of the present invention will become apparent from the following detailed description considered in connection with the accompanying drawings which disclose an embodiment of the present invention. It should be understood, however, that the drawings are designed for the purpose of illustration only and not as a definition of the limits of the invention.

In the drawings, wherein similar reference characters denote similar elements throughout the several views:

FIG. 5 is a perspective view of a first embodiment of the toothed belt with transport teeth on the conveying surface according to the invention;

FIG. 6 is a perspective view of a second embodiment of the toothed belt with transport slots on the conveying surface according to the invention; and FIG. 7 is a perspective view of a third embodiment the toothed belt with molded SAP-material receiving deepenings on the conveying surface according to the invention.

DETAILED DESCRIPTION OF PREFERRED EMBODIMENTS

Figure 1:
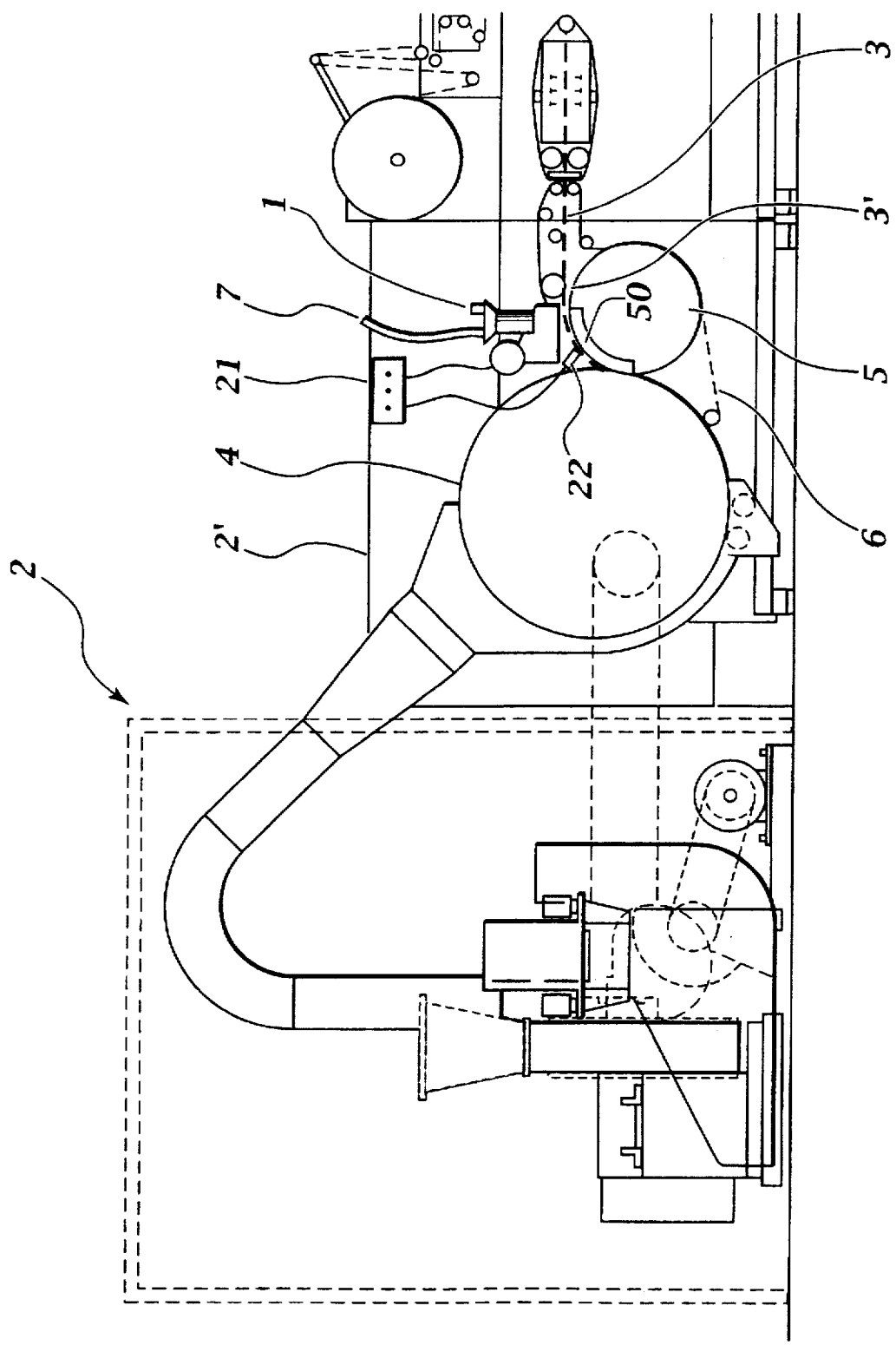
FIG. 1 is a lateral view of a flake-cushion forming station of a machine for producing sanitary napkins, with the sprinkling device according to the invention.

Referring now to FIG. 1, a sprinkling device 1 arranged above a material web 3 in a flake cushing forming station 2 of a sanitary napkin machine. Sprinkling device 1 is transversely displaceable with respect to material web 3 and adjustably mounted on a frame wall 2' with a spacing D (FIG. 2) from material web 3 by means of fixing and guiding elements (not shown). A pipeline 7 from a conveyor system and a collection container (not shown) feeds sprinkling device 1.

Material web 3 may consist of the individual suction cores 3', or of a continuous flake belt 3" (FIG. 2), which is only later separated to the individual suction cores 3'. Material web 3 is shaped on a molding device 4, and is passed at a continuous speed under sprinkling device 1, around a drum 5, and sprinkled section by section with SAP-material in predetermined areas during operation of the sanitary napkin machine. A suction chamber 50 is arranged underneath material web 3 and transport belt 6 opposite sprinkling device 1. Suction chamber 50 fixes the SAP-material onto material web 3 by aspirating sprinkled-on SAP-material into material web 3.

Figure 2:
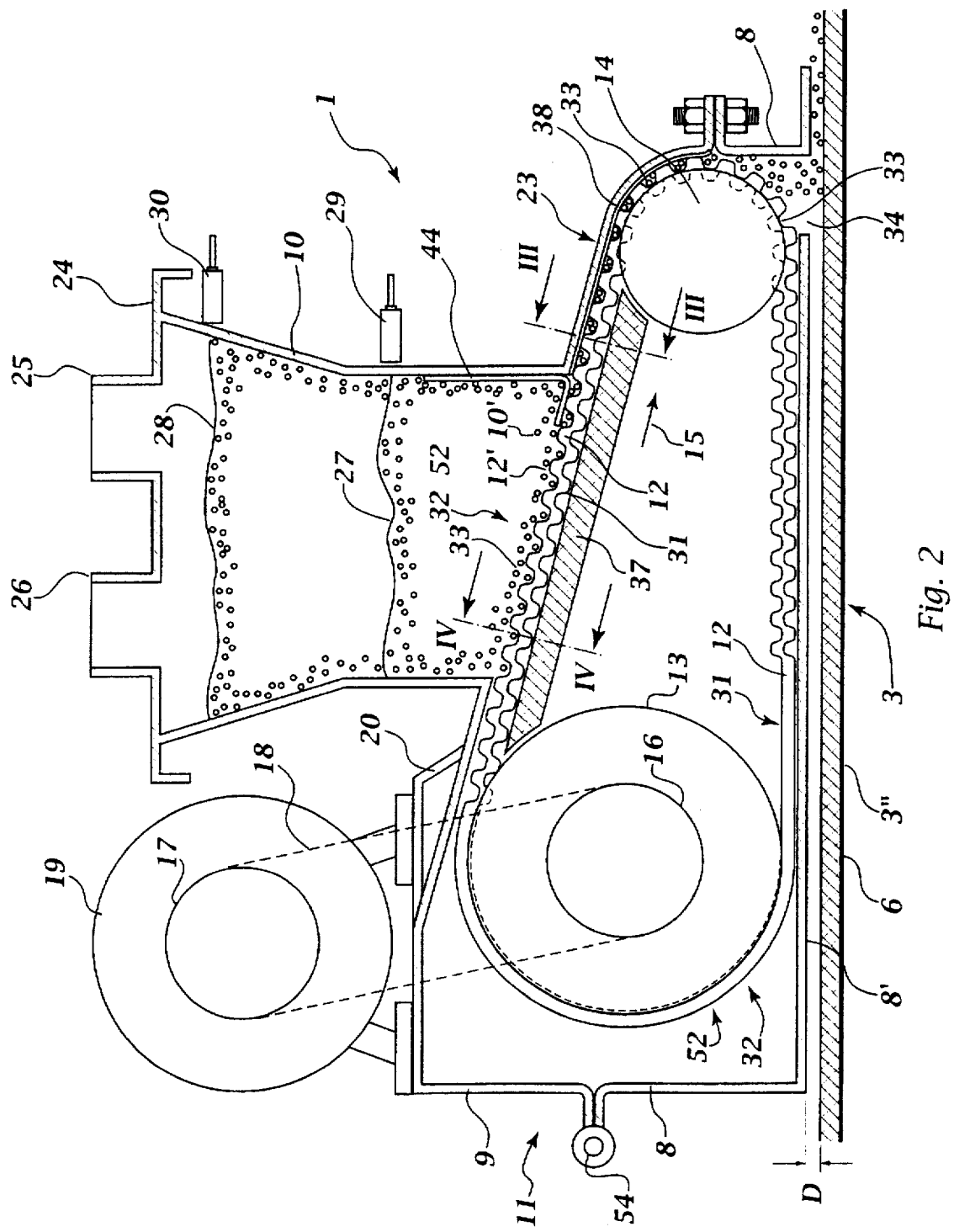
FIG. 2 is a sectional view of the sprinkling device according to the invention.

The basic structure of sprinkling device 1 is shown in FIG. 2. A conveyor system 23 is arranged in a closed housing 11 having a bottom part 8 and a top part 9. Top part 9 supports a supply container 10. Conveyor system 23 consists of a toothed belt 12 revolving in an endless loop around two cogs 13 and 14. Cogs 13 and 14 are rotatably supported in housing 11 by means of axles not shown. Toothed belt 12 is driven by cog 13 in direction 15. Cog 13 driven by a stepping motor 19 via driving gears 16 and 17, and an envelope driving element 18, such as, for example a belt, chain or any other suitable driving element. Stepping motor 19 is mounted on top part 9 by means of a console 20 and is controlled by a controlling device 21 (FIG. 1). Controller 21 utilizes at least one sensor 22, which monitors the position and the presence of suction cores 3'. Toothed belt 12 and envelope driving element 18 are tensioned in any suitably known technical manner.

Supply container or hopper 10 has a bottom-side opening 10', which is closed by top strand 12' of the toothed belt 12. The top side of supply container 10 is closed with a cover 24, which has a short outlet pipe 25 for air and a short inlet pipe 26 for SAP-material. Pipeline 7 (FIG. 1) feeds into inlet pipe 26. The minimum and maximum filling levels 27 and 28, respectively, of supply container/hopper 10 is monitored by means of sensors 29 and 30, respectively. Sensors 29 and 30 provide signals for controlling the conveyor system, such that the actual level of SAP-material within the supply container is always between the minimum and maximum filling levels 27 and 28, respectively.

The SAP-material falls through bottom side opening 10' of supply container 10 by means of gravity, and comes into contact with top strand 12'. Conveying surface 32 is specifically shaped for enabling the volumetrically-exact transport of SAP-material. The conveying surface 32 being opposite the toothed driving surface 31, which engages cogs 13 and 14 (See FIG. 5). Conveying surface 32 has conveying troughs 33 with an outer surface 52. Conveying troughs 33 are filled with SAP-material by gravity which is conveyed in the running direction 15 of toothed belt 12 around cog 14 to a discharge slot 34 arranged in the bottom 8' of bottom part 8. SAP-material is ejected from conveying troughs 33 through slot 34 by the force of gravity and the centrifugal force produced on rotating cog 14 and thereby sprinkles SAP-material onto material web 3. Excess SAP-material protruding beyond the teeth 52 of conveying surface 32 is retained within supply container 10 by an adjustable cleaning scraper 44 arranged on the inside wall in supply container 10. Cleaning scraper 44 is disposed on the downstream inside wall of supply container 10 such that it acts against the direction 15 of belt 12. In addition, scraper 44 assures that each conveying trough 33 has an equal amount of SAP-material for discharge.

FIGS. 5 to 7 show three embodiments of conveying surfaces 32, 132, and 232, and the respective conveying troughs 33, 133, and 233. Thus, the metered application of SAP-material can be controlled by adjusting the size and shape of the conveying troughs.

FIG. 5 shows a first embodiment of toothed belt 12, whose conveying surface 32 has teeth 52 whose gaps serve as conveying troughs 33. It is possible in connection with this variation to uniformly apply more or less SAP-material per application area by varying the speed of the intermittently-driven toothed belt 12. Thus, the content of a greater or lesser number of conveying troughs 33 can be sprinkled per application area to material web 3. The material web 3 being continuously passed beneath sprinkling device 1 in the operating cycle of the sanitary napkin machine.

FIG. 6 shows a second embodiment of a toothed belt 112 with an hour-glass like configuration of slot-like conveying troughs 133 arranged transversely relative to toothed belt 112 on conveying surface 132. Conveying troughs 133 may also be designed with different depths. This configuration results in a screened, hour-glass like SAP-material application on material web 3. In this connection, toothed belt 112 is driven intermittently in the operating cycle of the sanitary napkin machine.

FIG. 7 shows a third embodiment of a toothed belt 212 having a through-extending hour-glass like deepening as conveying trough 233 on its conveying surface 232. Conveying trough 233 also may have a profiled bottom. Toothed belt 212 also requires an intermittent drive in the operating cycle of the sanitary napkin machine.

Conveying surfaces 32, 132 and 232 of toothed belts 12, 112 and 212, respectively, have lateral flattenings or recesses 34 and 35 of the same width, along the lateral edges of the belts. Recesses 34 and 35 are adjacent teeth 52, and outer surfaces 152 and 252, and thereby limits the widths 36, 136 and 236, of the respective conveying surfaces.

Figure 3:
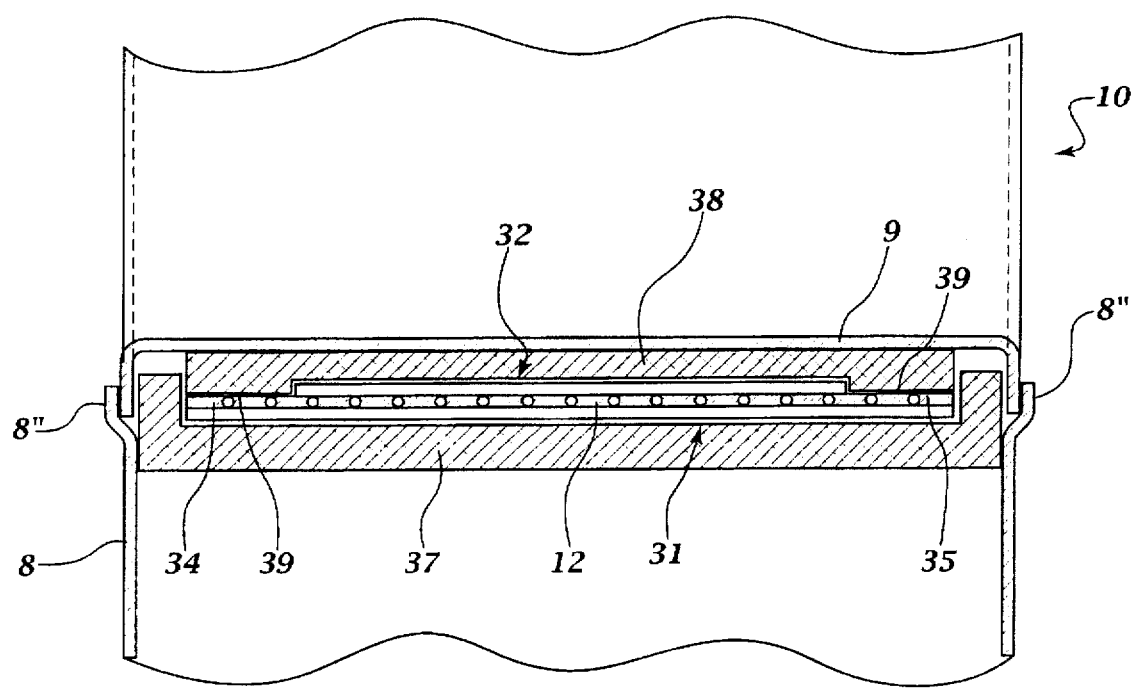
FIG. 3 is a cross-sectional view of the sprinkling device of the invention taken along line III—III of FIG. 2.
Figure 4:
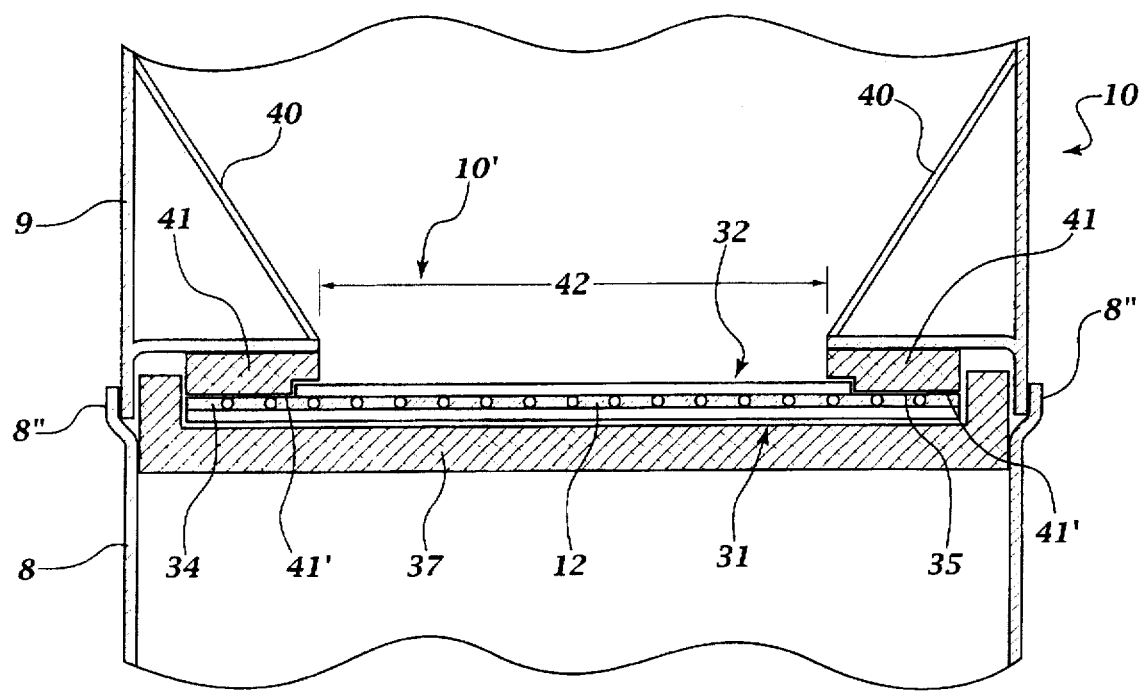
FIG. 4 is a cross-sectional view of the sprinkling device of the invention taken along line IV—IV of FIG. 2.

Between cogs 13 and 14, toothed belt 12 is supported by a slide guide 37 which, as shown in FIGS. 3 and 4, extends around belt 12 beyond top strand 12' from driving surface 32 in the form of a "U", and supports the strand against the filling weight of supply container 10. Slide guide 38, which is also U-shaped is exchangeably disposed above toothed belt 12. Slide guide 38 extends from supply container 10 around cog 14 up to and across the zone of separation between the bottom and top parts 8 and 9 of housing 11. Slide guide 38 covers teeth 52 of toothed belt 12, while at the same time closing off conveying troughs 33, and thus prevents SAP-material from accidentally escaping during transport from supply container 10 to discharge slot 34. In addition, leg-like extensions 39 of slide guide 38 and lateral flattenings 34 and 35 of toothed belt 12 jointly form lateral sealings.

Strips 41 (FIG. 4) are exchangeably and adjustably arranged within supply container 10, such that they limit the width 42 of opening 10' and thereby fixes the filling width for dispensing SAP-material. The leg-like extensions 41' engage lateral flattenings 34 and 35, and jointly form lateral sealings to close the sides of conveying troughs 33. Laterally-adjustable baffle plates 40 are arranged in supply container 10, and extend from oppositely-disposed side walls of supply container 10 in an inclined configuration up to the edges of opening 10'.

Slide guides 37 and 38 and strips 41 are manufactured from a material with a low coefficient of friction, and are adjustably and exchangeably disposed in housing 11. The adjustability and exchangability of slide guides 37 and 38, and strips 41 facilitate maintenance in order response to changes in wear and format. As described above, the housing is divided in order to permit a quick replacement of toothed belt 12, guides 38 and 39, and strips 41. In a preferred embodiment, bottom and top parts 8 and 9 are connected to each other on one side by a hinge or connection element 54 (FIG. 2) such that they can be folded open and closed. Lateral sealing elements 8" serve the purpose of providing a dust-free sealing of housing 11.

While several embodiments of the present invention have been shown and described, it is to be understood that many changes and modifications may be made thereunto without departing from the spirit and scope of the invention as defined in the appended claims.

What is claimed is:

1. A sprinkling device for the metered application of powdery to granulated materials such as super absorbing swelling substances (SAP-material) for disposal on predetermined surfaces of a continuously moving web of material within a machine for manufacturing hygienic products comprising:

a housing having an input for receiving SAP-material and an output slot for discharging metered amounts of SAP material onto the moving web of material, said input being an SAP-material supply hopper having an input for connection to an SAP-material source, and an open bottom for discharging the SAP-material;

a conveyor system disposed below said open bottom of said supply hopper, said conveyor system having;

at least two cogs spaced apart from each other on opposite sides of said open bottom of said supply hopper;

a conveyor drive coupled to one of said at least two cogs for driving said conveyor system;

a belt having lateral edges, a geared driving surface coupled around said at least two cogs, and a conveying surface, said conveying surface having conveying troughs for receiving and transporting the SAP-material from the supply hopper to the output, said conveying surface having a top surface that closes said open bottom of said supply hopper;

wherein said belt also comprises a lateral recess disposed along each of said lateral edges on said conveying surface of said belt; and a first slide guide extending between the open bottom of the supply hopper and the output slot, said slide guide enclosing said conveying surface of said belt and forming lateral seals with said recessed lateral edges of said belt.

2. The sprinkling device according to claim 1, wherein said conveying troughs of said belt comprises a plurality of teeth having gaps, said gaps serving as the conveying troughs.

3. The sprinkling device according to claim 1, wherein said conveying troughs of said belt comprise a plurality of equally spaced openings molded in said conveying surface, said conveying troughs enabling a volumetrically exact application of SAP-material.

4. The sprinkling device according to claim 1, further comprising a stepping motor coupled to the conveyor drive.

5. The sprinkling device according to claim 4, wherein the conveyor system is intermittently drivable by said stepping motor.

6. The sprinkling device according to claim 1, further comprising a U-shaped slide guide disposed between said at least two cogs and underneath said belt, said U-shaped slide guide being a second slide guide and extending around said lateral edges of said belt.

7. The sprinkling device according to claim 1, wherein the housing is divided into a bottom part and a top part.

8. The sprinkling device according to claim 7, further comprising hinge means coupled to said top and bottom parts.

9. The sprinkling device according to claim 1, further comprising a cleaning scraper disposed within the supply hopper directly above said conveying surface of said belt, said cleaning scraper freeing excess material from the conveying surface of said belt during rotation thereof around said at least two cogs.

10. The sprinkling device according to claim 1, further comprising strips disposed laterally above said belt, said strips fixing the width of the supply container opening, and forming lateral seals with said recessed lateral edges of said belt in the area of the open bottom of the supply container.

11. The sprinkling device according to claim 10, wherein said strips are replaceable with varying size strips.

12. The sprinkling device according to claim 10, further comprising adjustment means for adjustably changing the width of the supply container opening transversely with respect to said belt.

* * * * *